(12) United States Patent
Price et al.

(10) Patent No.: US 8,715,178 B2
(45) Date of Patent: May 6, 2014

(54) WEARABLE BADGE WITH SENSOR

(75) Inventors: David D. Price, Kennewick, WA (US);
Srinivasan Nallasivan, Charlotte, NC (US)

(73) Assignee: Bank of America Corporation, Charlotte, NC (US)

( * ) Notice: Subject to any disclaimer, the term of this patent is extended or adjusted under 35 U.S.C. 154(b) by 993 days.

(21) Appl. No.: 12/707,846

(22) Filed: Feb. 18, 2010

(65) Prior Publication Data

US 2011/0201959 A1  Aug. 18, 2011

(51) Int. Cl.
*A61B 5/00* (2006.01)
*G06F 19/00* (2011.01)
*G06F 17/27* (2006.01)

(52) U.S. Cl.
CPC .............. *G06F 19/00* (2013.01); *G06F 17/27* (2013.01)
USPC .......................................... 600/300; 434/156

(58) Field of Classification Search
USPC ................. 600/300, 301; 434/236, 156–185; 705/2–4
See application file for complete search history.

(56) References Cited

U.S. PATENT DOCUMENTS

| | | | |
|---|---|---|---|
| 5,800,337 A | 9/1998 | Gavish | |
| 6,308,154 B1 | 10/2001 | Williams et al. | |
| 6,520,905 B1 * | 2/2003 | Surve et al. | 600/26 |
| 6,542,602 B1 | 4/2003 | Elazar | |
| 7,346,186 B2 | 3/2008 | Sharoni et al. | |
| 7,386,105 B2 | 6/2008 | Wasserblat et al. | |
| 7,577,246 B2 | 8/2009 | Idan et al. | |
| 7,676,372 B1 * | 3/2010 | Oba | 704/271 |
| 7,959,567 B2 | 6/2011 | Stivoric et al. | |
| 8,226,417 B2 * | 7/2012 | Mitsuyoshi | 434/236 |
| 2003/0059750 A1 | 3/2003 | Bindler et al. | |
| 2003/0139654 A1 | 7/2003 | Kim et al. | |
| 2003/0149344 A1 * | 8/2003 | Nizan | 600/300 |

(Continued)

FOREIGN PATENT DOCUMENTS

| | | |
|---|---|---|
| DE | 4221526 A1 | 1/1994 |
| DE | 10152852 A1 | 5/2003 |

(Continued)

OTHER PUBLICATIONS

"Anger Management," http://spectrum.ieee.org/at-work/tech-careers/anger-management, Apr. 2005.

(Continued)

*Primary Examiner* — Bill Thomson
*Assistant Examiner* — Bobby Soriano
(74) *Attorney, Agent, or Firm* — Weiss & Arons LLP; Michael A. Springs, Esq.

(57) ABSTRACT

Systems and methods for a wearable badge with a sensor are provided. The badge may include a sensor. The sensor may monitor a response of a wearer. The sensor may monitor a response of an individual facing the wearer. A reference index may correlate the response to a known condition. A processor device may detect the known condition or a threshold number of known conditions. The processor may relate the known condition to feedback. A feedback mechanism may provide the feedback to the wearer. The feedback mechanism may provide the feedback to the individual facing the wearer. The feedback may be provided based on the known condition. The feedback may be configured to provide guidance to the wearer and the individual facing the wearer. The feedback may be based on the threshold number.

21 Claims, 6 Drawing Sheets

(56) References Cited

U.S. PATENT DOCUMENTS

| | | | |
|---|---|---|---|
| 2003/0227386 A1* | 12/2003 | Pulkkinen et al. | 340/573.1 |
| 2004/0018476 A1 | 1/2004 | LaDue | |
| 2004/0117212 A1 | 6/2004 | Kong et al. | |
| 2004/0147814 A1 | 7/2004 | Zancho et al. | |
| 2005/0148283 A1* | 7/2005 | Schwalm | 446/485 |
| 2005/0154264 A1 | 7/2005 | Lecompte et al. | |
| 2005/0192514 A1 | 9/2005 | Kearby et al. | |
| 2005/0288601 A1 | 12/2005 | Wood et al. | |
| 2006/0234201 A1 | 10/2006 | Pierson, III et al. | |
| 2006/0277065 A1 | 12/2006 | Guten et al. | |
| 2006/0293921 A1 | 12/2006 | McCarthy et al. | |
| 2007/0050215 A1* | 3/2007 | Kil et al. | 705/3 |
| 2007/0123794 A1 | 5/2007 | Togino | |
| 2007/0185533 A1 | 8/2007 | Gerdes | |
| 2008/0131851 A1 | 6/2008 | Kanevsky et al. | |
| 2008/0146890 A1 | 6/2008 | LeBoeuf et al. | |
| 2008/0208015 A1 | 8/2008 | Morris et al. | |
| 2008/0214903 A1 | 9/2008 | Orbach | |
| 2009/0037225 A1 | 2/2009 | Burchianti, II et al. | |
| 2009/0206992 A1* | 8/2009 | Giobbi et al. | 340/5.74 |
| 2009/0318773 A1* | 12/2009 | Jung et al. | 600/300 |
| 2010/0015583 A1 | 1/2010 | Leuthardt et al. | |
| 2010/0102929 A1* | 4/2010 | Haumann | 340/5.81 |
| 2010/0120000 A1 | 5/2010 | Bellamy et al. | |
| 2010/0169220 A1* | 7/2010 | Choing et al. | 705/51 |
| 2011/0004276 A1* | 1/2011 | Blair et al. | 607/60 |
| 2011/0015497 A1* | 1/2011 | Eggenberger et al. | 600/301 |
| 2011/0151418 A1 | 6/2011 | Delespaul et al. | |
| 2011/0172500 A1* | 7/2011 | Van Dooren et al. | 600/300 |
| 2011/0183305 A1* | 7/2011 | Orbach | 434/236 |
| 2012/0323087 A1* | 12/2012 | Leon Villeda et al. | 600/301 |

FOREIGN PATENT DOCUMENTS

| | | |
|---|---|---|
| GB | 2331201 | 5/1999 |
| GB | 2393605 A | 3/2004 |
| JP | 2005046305 A | 2/2005 |
| JP | 2005237668 A | 9/2005 |
| WO | WO 9701984 A1 | 1/1997 |
| WO | WO 2006090371 A2 | 6/2006 |
| WO | WO 2009045449 A1 | 4/2009 |
| WO | WO 2009147625 A1 | 12/2009 |

OTHER PUBLICATIONS

"Meeting Mediator: Enhancing Group Collaboration using Sociometric Feedback" (http://vismod.media.mit.edu//tech-reports/TR-621.pdf), MIT Media Lab, Cambridge, Massachusetts, 2008.

"Sociometric Badges: State of the Art and Future Applications", MIT Media Laboratory, Boston, Massachusetts, 2007.

"Sociometric Feedback: Bringing Social Signals to Telepresence" (http://research.microsoft.com/en-us/events/nft2010/kimsociometric.pdf), MIT Media Laboratory, Boston, Massachusetts, 2008.

* cited by examiner

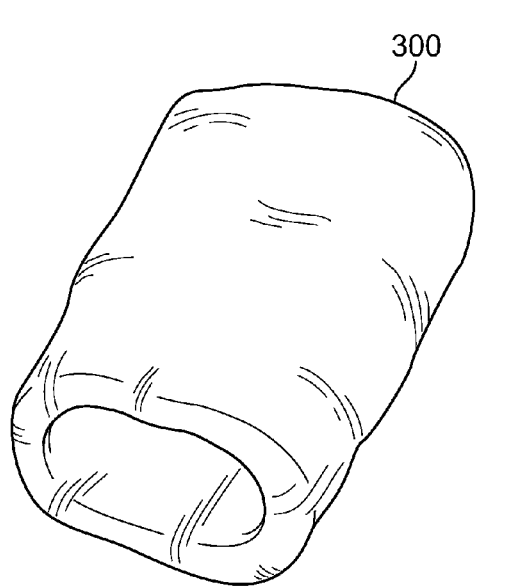
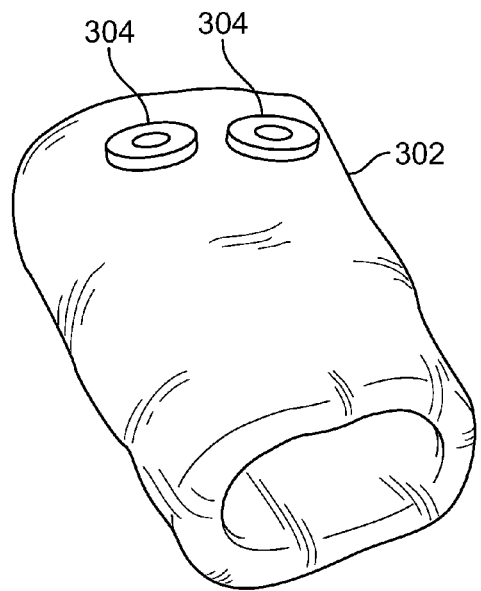
FIG. 3A
FIG. 3B
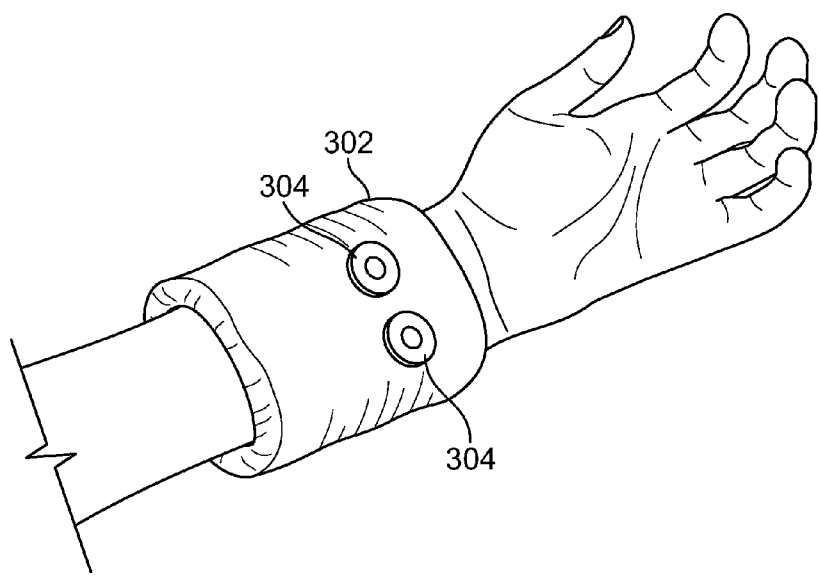
FIG. 3C

Front

Hello My Name Is: — 504
— 500
— 502

Back

— 508
— 506
— 570

WEARABLE BADGE WITH SENSOR

FIELD OF TECHNOLOGY

Aspects of the invention relate to inducing change in a performance characteristic.

BACKGROUND

Emotions play an important role in the outcome of interpersonal interactions. In large call centers or industries that are reliant on quality customer service, emotional stability of customer service representatives is important for successful resolutions of customer concerns. On one hand the calm demeanor of an employee can quickly allay a customer's feelings of hostility. On the other hand, one angry party can easily influence a conversation, making it difficult for either party to reach a clear thought out decision.

Changes in emotional equilibrium may inhibit critical thinking, problem solving ability, and conflict resolution skills. An agitated employee may find it difficult to think clearly, impairing his or her ability to complete an otherwise simple task. Management that is unaware of emotional challenges facing employees cannot provide training that is needed to improve performance. New members added to an existing team may need additional assistance adapting to the team environment, culture, or other team members. Other members of the team may need help adjusting to the presence of a new member.

However, emotional changes can be subtle and one may not be aware of an emotional change until after it has occurred. Even if one is aware of a emotional change, it is usually difficult for an individual to identify the change, articulate exactly what the change represents or how to return to equilibrium. Nevertheless, the human body will react physiologically during an emotional change, and a change in a performance characteristic may be detected before the individual can explain or understand the bodily reaction. Changes in a performance characteristic may be observed and empirically associated with emotional changes.

It is important to detect and respond to both positive and negative emotional changes. Positive aspects of a work environment may stimulate productive emotional changes in individuals. Emotions such as joy or perhaps the absence of emotional swings can lead to higher levels of productivity and efficiency. In some scenarios it may be beneficial to induce these positive and productive emotional changes. In some scenarios it may be beneficial to express exuberance. For example, an unemotional employees may appear indifferent or uncaring to customers and coworkers.

However, an individual may be unaware of changes in his emotional state or methods by which he can induce a productive emotional state. Interventional feedback providing relevant information at critical junctures at or close to an emotional change may provide such awareness, induce productive emotions and provide other benefits.

Accordingly, it would be desirable to provide systems and methods to detect human emotional changes and provide responsive interventional feedback.

SUMMARY OF THE INVENTION

It is an object of this invention to provide systems and methods to detect human emotional changes and provide responsive interventional feedback.

BRIEF DESCRIPTION OF THE DRAWINGS

The objects and advantages of the invention will be apparent upon consideration of the following detailed description, taken in conjunction with the accompanying drawings, in which like reference characters refer to like parts throughout, and in which:

FIG. 3A shows illustrative apparatus in accordance with the principles of the invention;

FIG. 3B shows further illustrative apparatus in accordance with the principles of the invention;

FIG. 3C shows still further illustrative apparatus in accordance with the principles of the invention;

DETAILED DESCRIPTION OF THE INVENTION

Figure 1:
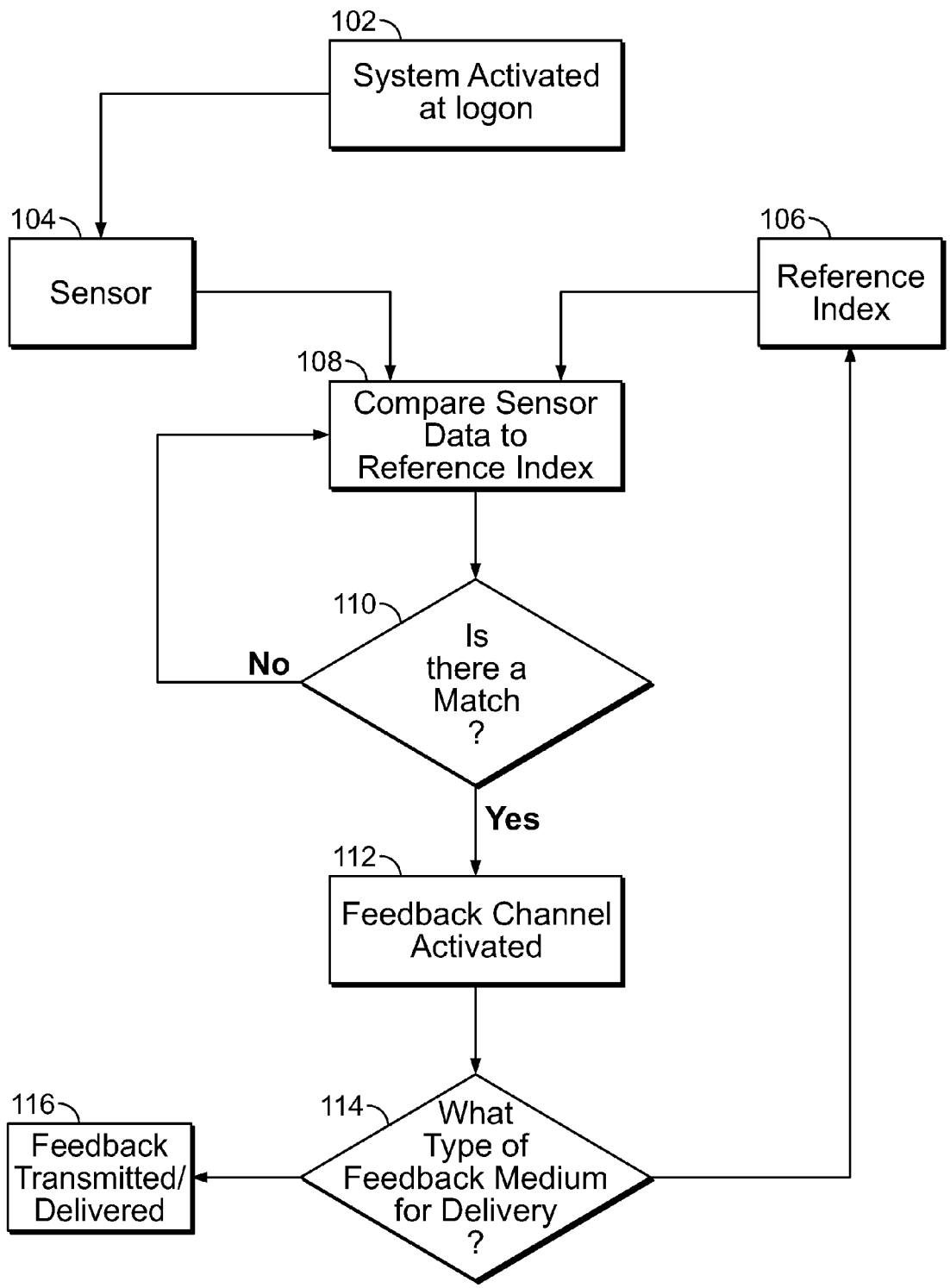
FIG. 1 shows an illustrative flow diagram of steps for measuring, monitoring, and providing feedback in response to emotional change.

Systems and methods for inducing a change in a performance characteristic are provided. The performance characteristic may correspond to an emotional state of a dialogue participant. The dialogue participant may be an individual participating in a conversation. The conversation may be any suitable type of conversation. For example the conversation may take place in person, over the telephone, by text message, chat room, instant message, or any other suitable forum. The participant may be a call center agent, a sale representative, a customer service associate, a customer, a prospective customer, a person requesting assistance, or any other suitable participant. For the purposes of this description, the participant will be referred to as the "respondent."

In some embodiments, the systems and methods may involve providing appropriate feedback to the respondent to restore the respondent's equilibrium, induce productive emotions in the respondent or hand off volatile interactions to more experienced personnel. Some embodiments may include systems and methods for detecting emotional change, forms of feedback, and apparatus and methods for delivering feedback.

Systems and methods according to the invention may include a sensor configured to sense a performance characteristic indicative of an emotional change. The sensor may detect the performance characteristic even if the monitored individual is not consciously aware of the change. Different sensors may be used to detect different physiological changes, whether they represent positive or negative emotional changes. The different sensors may be used independently or together. In some embodiments, two or more sensors may be incorporated into one device.

In some embodiments, two or more different sensors may be used to monitor two or more respective different performance characteristics. For example, a keyboard-deployed finger- or hand-temperature sensor may be used in conjunction with an eye-movement sensor. Such embodiments may process inputs from the two or more sensors to determine emotional state.

Illustrative performance characteristics may include sweatiness of the palms, heart rate, body temperature, body motion, eye movement or facial expression, or speech patterns. Moist palms may signify apprehension, an increased heart rate excitement, and rolling one's eyes indicates contempt. Fidgeting in one's chair may indicate uneasiness or apprehension. Cold hands typically signify stress and high body temperature is associated with anger. The facial expressions or eye movements of others in the course of a personal interaction may indicate whether one individual is being warmly accepted by another. When speaking repetition of particular words, or how many times parties interrupt each other may indicate frustration or anger.

Some embodiments may include sensors built into headsets typically worn by call center personnel, sensors built into a seating apparatus, sensors incorporated into articles of clothing, a microphone to capture speech, an image capturing device, or any sensor suitable for sensing a performance characteristic.

For example, a sensor measuring hand temperature may be integrated into a computer mouse or keyboard. For average individuals if hand temperature falls below 85 degrees Fahrenheit, it is likely that the individual is under stress. The sensor may utilize a thermo-resistor whose resistance, and voltage measured across the thermo-resistor vary with temperature. A change in hand temperature would cause a measurable change in the voltage output by the sensor.

The systems and methods may also include a machine readable memory configured to store a reference index of a performance characteristic. The reference index may associate sensor output to a performance characteristic. and in turn, associate the performance characteristic to a known emotional state. Associations between a performance characteristic and an emotional state may be based on empirical studies, case studies, historical data, theory or any other suitable information. Associations within the reference index may be implemented using pointers or any other suitable data structure.

For example, if a sensor measures hand temperature, the reference index may contain an array of voltages associated with temperature values, and the temperature values associated with different emotional states. For example a reference index for hand temperature may associate 0.5V with a temperature of 70 degrees Fahrenheit. Within the reference index, the entry of 70 degrees Fahrenheit, a low hand temperature, will be associated with the emotion of stress.

The output voltage of the sensor would be compared to the voltage values contained in the reference index. If within the reference index the output voltage of the sensor is associated with a low temperature, and within the reference index a low hand temperature is associated with the emotion of stress, it is likely a respondent is experiencing stress, and an emotional change has been detected. If within the reference index the output voltage of the sensor is associated with a high temperature, such as higher than 90 degrees Fahrenheit, and within the reference index a high hand temperature is associated with calmness and relaxation, it is likely the respondent is calm and relaxed. If within the reference index the output voltage of the sensor is associated with a very high temperature, such as higher than 99 degrees Fahrenheit, and within the reference index a very high hand temperature is associated with extreme relaxation, the respondent is likely daydreaming.

In some embodiments, the sensor may monitor human speech, outputting a voltages corresponding to tone, pitch, amplitude or frequency or a speech pattern. The reference index may associate the voltage output of the sensor with a speech pattern, and within the reference index a specific speech pattern may be associated with a particular feeling or emotional state.

For example, in the course of a conversation, a sensor monitoring the speech of a respondent may output a series of voltages. These voltages may be compared to the reference index, where they may be associated with a high frequency of mid sentence interruptions. A speech pattern exhibiting a high frequency of mid sentence interruptions may in turn be associated within the reference index with the emotion of anger or frustration.

The reference index may be stored on an independent storage medium or accessed through a network. For example, data can be stored remotely and accessed over the internet. Network access allows the reference index to be easily updated or customized at one central location.

The sensor output and the reference index may interact using a processor device configured to compare the sensor output to a array of like values within the reference index. If a matching data entry is found in the reference index, the processor device may continue to search for and follow subsequent associations between the reference index entry identical to the sensor output and additional entries in the reference index associated with the entry identical to the sensor output. Additional entries may include a performance characteristic. Within the reference index, a performance characteristic may subsequently be associated with an emotional state. In some embodiments, output from the sensor or data from the reference index or both may be transmitted to the processor device using a wired or wireless link or combination thereof.

If the sensor output contains information associated within the reference index with an emotional state, an emotional state has been detected. The state may signify a change relative to a previous state. Once a change has been detected, a feedback channel may be activated to transmit feedback information based on the change.

The feedback information may be stored locally, remotely, or accessed through a network. Network access allows retrieval of targeted feedback residing on remote systems. The feedback information may take the form of text, audio, visual display or combination thereof.

The feedback information may include conflict resolution strategies, advice on how to return to emotional equilibrium, information on participants emotional state or any other suitable information. Feedback may be provided from stored feedback messages, which may include text, graphics, audio and video information. Feedback may be provided from a live source. For example, a human supervisor may provide the respondent with one or more textual, audio or video messages. In some embodiments, the supervisor may provide a combination of live and stored feedback messages.

Feedback may be delivered to a participant in real time, at a later date, or even preemptively. For example, if the emotion detected corresponds to anger, an electronic signal may activate a visual display informing the individual anger has been detected. Emotional awareness is intrinsically valuable. Once notified one can try to return to a more productive state.

If anger is detected in a respondent, suggestions on how to cope with anger may be transmitted. A message can be sent suggesting a phrase known to diffuse tension when conveyed or read. In other embodiments feedback information may be expert advice, biofeedback techniques, or any communication fostering productive emotions.

In some embodiments, feedback information may be transmitted as an interactive chat dialogue. Additional feedback information may be transmitted after receiving a response to previously transmitted feedback information.

In some embodiments, feedback information may be transmitted to a non-participating third party. For example, feedback may be transmitted to a participant's supervisor. The feedback may indicate an emotional change that the sensor detected in the participant. Once notified, the supervisor may give the participant immediate attention and guidance or take control of the participants dialogue. After feedback has been transmitted to the non-participant third party, additional feedback may be transmitted to the participant. In some embodiments discretionary feedback may include constructive criticism, or rewards for exceptional performance.

The systems and methods may include a respondent input feature. Using the respondent input feature, the respondent may edit stored feedback to tailor the feedback messages that will be presented to the respondent when triggering physiological circumstances occur. In some embodiments, the respondent may store messages for a supervisor to consider in connection with the supervisor's provision of feedback to the respondent when the triggering physiological circumstances occur.

Some embodiments may include a feedback log. The feedback log may include for each feedback message provided to the respondent a record that identifies the feedback message, the date and time that the feedback message was provided to the respondent, a sample of the physiological data (raw, processed or otherwise) collected prior to the provision of the feedback message, a sample of the physiological data (raw, processed or otherwise) collected simultaneous the provision of the feedback message, a sample of the physiological data (raw, processed or otherwise) collected after the provision of the feedback message and any other suitable information.

The feedback log may be used by a processor to meter feedback messages to the respondent to reduce the likelihood that a feedback message will be presented to a respondent more than a limited number of times. In some embodiments, correlative algorithms may be implemented to correlate one or more feedback messages with corresponding emotional states. For example, one feedback mechanism may appear to help a respondent return to equilibrium. Another feedback mechanism may appear to not help the respondent return to equilibrium. Similarities or differences between physiological responses sensed during an in-progress dialog and historical physiological patterns for the same respondent may be used to help select appropriate and successful feedback messages for the in-progress dialog.

In some embodiments, the systems and methods may be used as a tool to "on-board" and train new hires. Instead of assigning a senior employee to take time training a new hire, the systems and methods may provide feedback and suggestions directly to the new hire. Upon detection of an emotional change, suggestions may be made to the new hire on how to improve performance. The feedback may include directions, a policy reminder, a suggestion to seek help, an identity of an individual from whom assistance may be obtained, a message alerting a supervisor to give additional guidance or any other suitable information. Using the systems and methods, the on-boarding process may be fully automated, using minimal human resources.

In some embodiments, a sensor may be incorporated into a badge worn by new hires. The badge may record physiological data such as temperature or blood pressure and at the same time identify the employee as a "new hire" to coworkers. The badge may also monitor performance characteristics of a individual or group facing the badge wearer. Feedback may then be transmitted to either the wearer or persons interacting with the wearer, streamlining the integration of new hires.

More generally, feedback may be used to "coach" the participant. When an emotional change is detected, feedback may remind the participant of protocol, workplace rules, or best practices in stressful circumstances. Additional embodiments may include alerting a supervisor who can come in person to assist the individual, or remotely join an interaction.

The systems and methods may be used to gauge the effectiveness of new policies. If there are increased levels of emotional change following implementation of new rules, feedback may be transmitted to rule makers. The rule makers may then adjust the policy accordingly. In some embodiments, feedback information may be transmitted to rule followers to ease implementation of new policy. Feedback transmitted to rule followers may include reminders of a new policy before a specific task is performed.

In some embodiments, the reference index of a respondent or a class of respondents may include additional entries associates with the emotional state entries. The additional associated entries may include a time and date stamp of when a specific emotional change was last detected, the identity of a participant whose physiological data resulted in detection of an emotional change, a running total of the emotional changes of a participant or class of participants, or any other suitable information. Additional associated entries may be further associated with different additional entries. Specific feedback addressing an emotional change may be transmitted based on these additional associations.

For example, if within a reference index an emotional state entry is associated with a running total of emotional changes detected in the respondent, the running total may be subsequently associated within the reference index with a threshold number. The processor device may determine if the running total entry exceeds the threshold number entry. If the running total is larger the respondent has triggered excessive associations between sensor output and an emotional state. Because of the excessive associations, higher level intervention may be implemented. Higher level intervention may include additional training, a location change, or personal consultation by a supervisor.

In some embodiments, if a class of respondents running total number entry exceeds a threshold number entry, the next time a class member triggers an association between sensor output and an emotional state, the feedback channel may skip a traditional feedback message, instead directly alerting a supervisor or delivering specialized feedback. Specialized feedback may include any suggestions that are known to be helpful to class members.

In some embodiments, within a reference index, an emotional state entry may be associated with a time and date stamp. The time and date stamp may be subsequently associated with a different running total entry and a different threshold number. If members of a defined class exceed the threshold number of emotional changes during a time period, feedback may be transmitted prior to the start of the time period.

For example, associated entries within the reference index may indicate respondents experience a high frequency of emotional change close to the end of a workday. Feedback information may be transmitted preemptively earlier in the day to give prepare class members for future dialogues. The preemptive feedback may include advice or tips on how to cope with increased stress at the end of a work day.

As a further illustration, associated entries within the reference index may indicate a change in disposition among a class of call center respondents. The feedback information may put management on notice to search for what is causing the change. Management may find that callers in a particular segment outside of the call center area of training may trigger such change. Feedback may then be transmitted to class members in the form of training modules that explain why they are experiencing the change.

Additional associated entries within the reference index may indicate that when an incoming call originates from, a particular segment outside of the call center area of training, preemptive or concurrent instructions may be given, coaching employees on how they can best adapt to avoid a change in disposition.

In some embodiments, call center management may respond to emotional changes in callers in a particular segment outside of the call center area of training. This is particularly useful for call centers that receive international calls. Feedback information transmitted to the management may show that callers from Sydney, Australia have difficulty resolving their concerns with a particular subset of employees working out of Belarus. A high frequency of emotional changes detected on the Sydney/Belarus calls may indicate a likelihood of low productivity and high levels of unresolved customer concerns.

These emotional changes may be detected by sensing the speech patterns of a customer calling the call center or of an employee responding to the call. Management may find that when Sydney calls are directed to a call center in London the rate or number of emotional changes decreases. Feedback that induces productive emotions may be transmitted to both Sydney customers and Belarus employees, in the form of redirecting Sydney calls to a different call center. A resulting decrease in emotional changes following the redirection of Sydney calls to London may indicate customer concerns are resolved quickly without adverse emotional changes in customers or call center employees.

Illustrative embodiments of apparatus and methods in accordance with the principles of the invention will now be described with reference to the accompanying drawings, which form a part hereof. It is to be understood that other embodiments may be utilized and structural, functional and procedural modifications may be made without departing from the scope and spirit of the present invention.

As will be appreciated by one of skill in the art, the invention described herein may be embodied in whole or in part as a method, a data processing system, or a computer program product. Accordingly, the invention may take the form of an entirely hardware embodiment, an entirely software embodiment or an embodiment combining software, hardware and any other suitable approach or apparatus.

Furthermore, such aspects may take the form of a computer program product stored by one or more computer-readable storage media having computer-readable program code, or instructions, embodied in or on the storage media. Any suitable computer readable storage media may be utilized, including hard disks, CD-ROMs, optical storage devices, magnetic storage devices, and/or any combination thereof. In addition, various signals representing data or events as described herein may be transferred between a source and a destination in the form of electromagnetic waves traveling through signal-conducting media such as metal wires, optical fibers, and/or wireless transmission media (e.g., air and/or space).

Processes in accordance with the principles of the invention may include one or more features of the process illustrated in FIG. 1. For the sake of illustration, the steps of the process illustrated in FIG. 1 will be described as being performed by a "system". The "system" may include one or more of the features of the apparatus that are shown in FIGS. 2-6 and/or any other suitable device or approach. The "system" may be provided by an entity. The entity may be an individual, an organization or any other suitable entity.

FIG. 1 shows illustrative steps that may be performed by some embodiments of the invention. For the purpose of illustration the steps will be described as being performed by or on a system in accordance with the principles of the invention.

Figure 4:
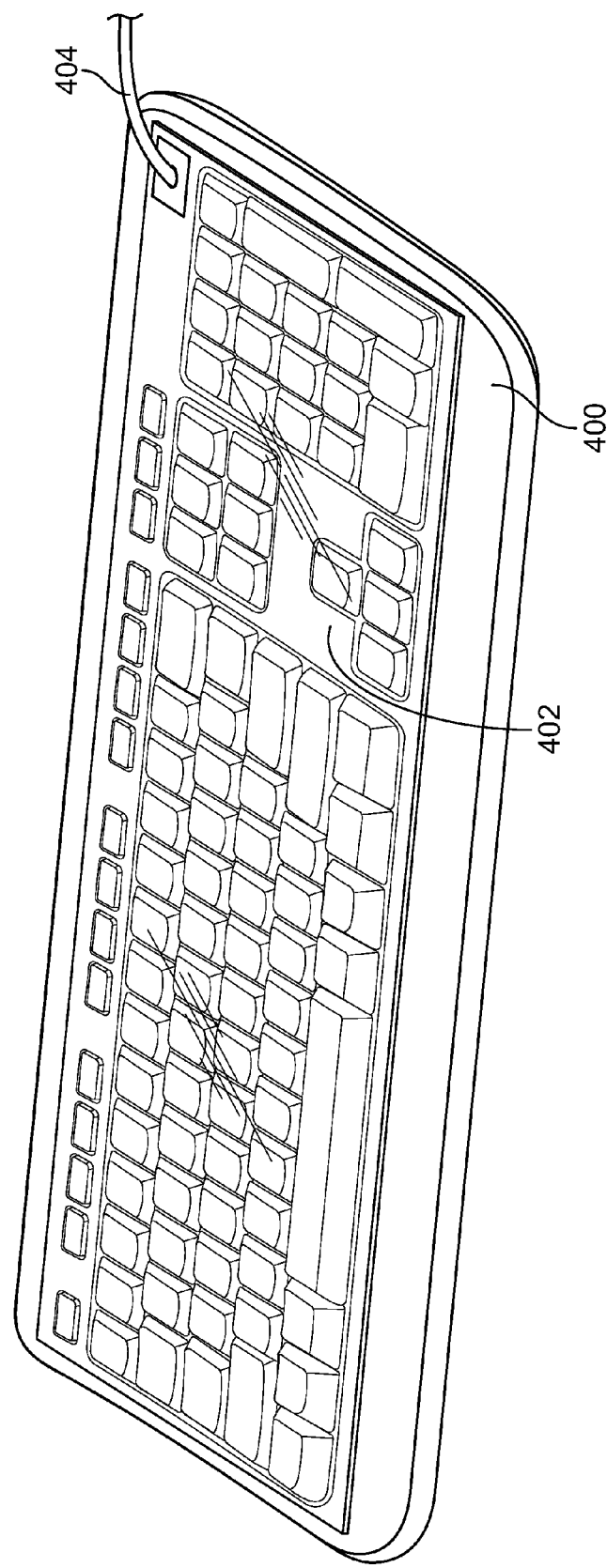
FIG. 4 shows yet further illustrative apparatus in accordance with the principles of the invention.
Figure 5:
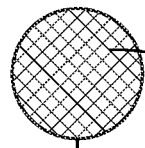
FIG. 5 shows yet further illustrative apparatus in accordance with the principles of the invention.

At step 102 an individual may activate the system. The activation may occur when an individual logs on to a personal computer. At step 104 a sensor may monitor and measure a set of performance characteristics. In some embodiments, the sensor may perform continuous monitoring. (FIG. 3-5 show illustrative embodiments of the sensor described in connection with step 104 (shown in FIG. 1).)

At step 106, as part of the activation process, a reference index may be loaded into a computer readable memory. The reference index may contain associations linking sensor output to an emotional state. The reference index may also include associations between an emotional state other relevant data.

Figure 2:
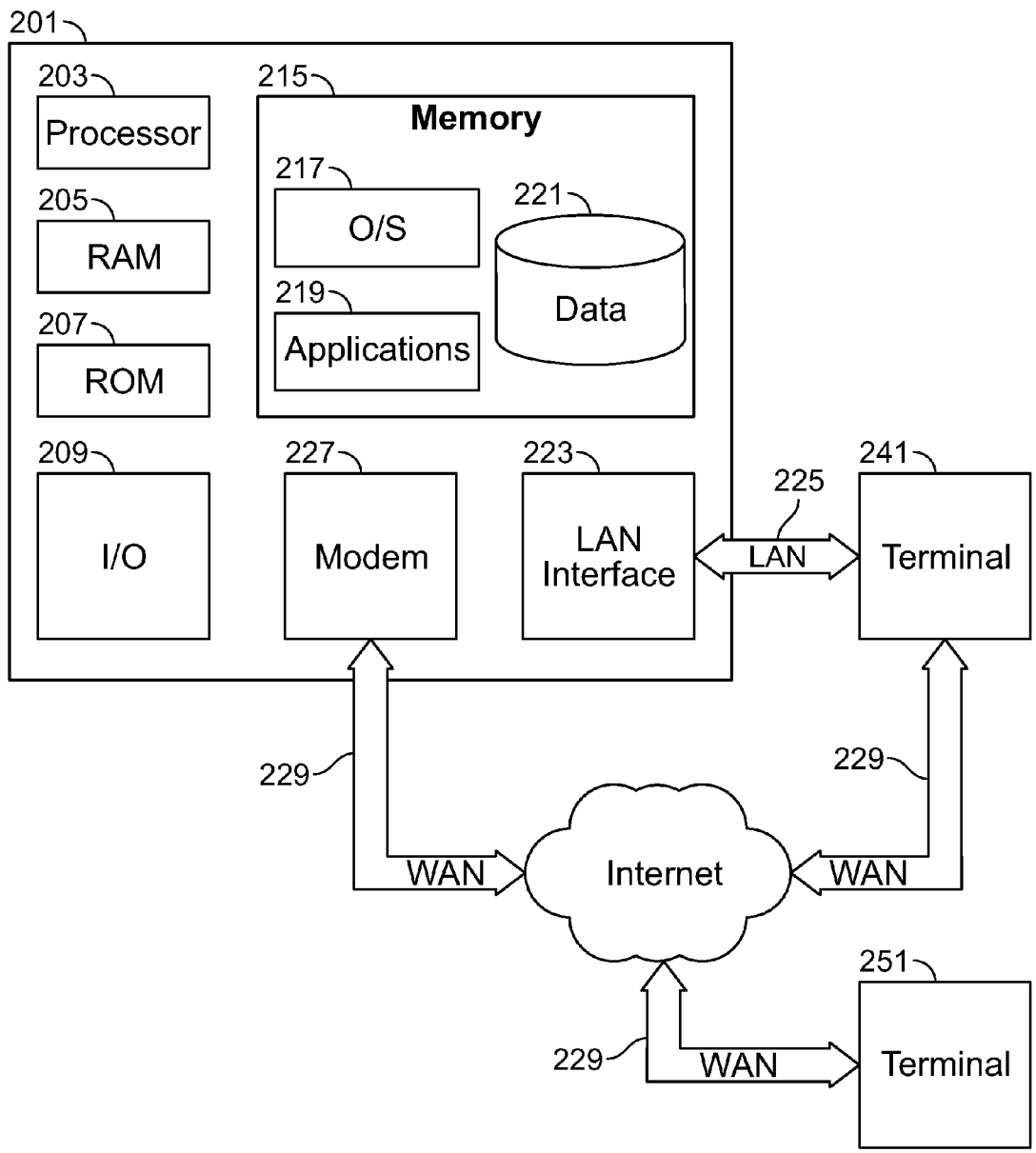
FIG. 2 shows a schematic diagram of a general purpose digital computing environment in which one or more aspects of the present invention may be implemented.

At step 108, the sensor data of step 106 and reference index of step 104 are compared using a processor device. (FIG. 2 shows an embodiment of a processor device that may be used to perform the comparison.) Data from steps 106 and 104 may be transmitted to the processor device through a remote or local subsystem via wired or a wireless links. The processor device itself may be a local or remote subsystem.

At step 110 the system determines if physiological data collected from the sensor matches an emotional state contained in the reference index. If a matching entry in the reference index is not found, the system returns to step 108, and continues to scan physiological data detected by the sensor. If a matching pattern is found, at step 112 a feedback channel is activated to transmit feedback information based on the emotional state detected.

At step 114, the system determines what type of feedback should be transmitted and an appropriate medium for transmission. Decision criteria may include associations contained in the reference index of step 106. Information received at step 114 may be used to update or add new association information to the reference index of step 106. Information added may include an indicator that a threshold number of emotional changes has been reached. If another iteration of FIG. 1 would be triggered, step 114 may then authorize transmission of different feedback in response to another identical emotional change.

At step 116 feedback is transmitted to the recipient. Information processed at step 114 will determine who receives the feedback and the medium for transmission. Examples may include an email message, a telephone call, a chat response or a visual icon.

One of ordinary skill in the art will appreciate that the steps shown and described herein may be performed in other than the recited order and that one or more steps illustrated may be optional. The methods of the above-referenced embodiments may involve the use of any suitable elements, steps, computer-executable instructions, or computer-readable data structures. In this regard, other embodiments are disclosed herein as well that can be partially or wholly implemented on a computer-readable medium, for example, by storing computer-executable instructions or modules or by utilizing computer-readable data structures.

FIG. 2 illustrates a block diagram of a generic computing device 201 (alternatively referred to herein as a "server") that may be used according to an illustrative embodiment of the invention. The computer server 201 may have a processor 203 for controlling overall operation of the server and its associated components, including RAM 205, ROM 207, input/output module 209, and memory 215.

I/O module 209 may include a microphone, keypad, touch screen, and/or stylus through which a user of device 201 may provide input, and may also include one or more of a speaker for providing audio output and a video display device for providing textual, audiovisual and/or graphical output. Software may be stored within memory 215 and/or storage to provide instructions to processor 203 for enabling server 201 to perform various functions. For example, memory 215 may store software used by server 201, such as an operating system 217, application programs 219, and an associated database 221. Alternatively, some or all of server 201 computer executable instructions may be embodied in hardware or firmware (not shown). As described in detail below, database 221 may provide centralized storage of sensor correlation constants, performance characteristic reference index values and emotional state information.

Server 201 may operate in a networked environment supporting connections to one or more remote computers, such as terminals 241 and 251. Terminals 241 and 251 may be personal computers or servers that include many or all of the elements described above relative to server 201. The network connections depicted in FIG. 2 include a local area network (LAN) 225 and a wide area network (WAN) 229, but may also include other networks. When used in a LAN networking environment, computer 201 is connected to LAN 225 through a network interface or adapter 223. When used in a WAN networking environment, server 201 may include a modem 227 or other means for establishing communications over WAN 229, such as Internet 231. It will be appreciated that the network connections shown are illustrative and other means of establishing a communications link between the computers may be used. The existence of any of various well-known protocols such as TCP/IP, Ethernet, FTP, HTTP and the like is presumed, and the system can be operated in a client-server configuration to permit a user to retrieve web pages from a web-based server. Any of various conventional web browsers can be used to display and manipulate data on web pages.

Additionally, application program 219 used by server 201 according to an illustrative embodiment of the invention may include computer executable instructions for invoking user functionality related to communication, such as email, short message service ("SMS"), and voice input and speech recognition applications.

Computing device 201 and/or terminals 241 or 251 may also be mobile terminals including various other components, such as a battery, speaker, and antennas (not shown).

The invention may be operational with numerous other general purpose or special purpose computing system environments or configurations. Examples of well known computing systems, environments, and/or configurations that may be suitable for use with the invention include, but are not limited to, personal computers, server computers, hand-held or laptop devices, mobile phones and/or other personal digital assistants ("PDAs"), multiprocessor systems, microprocessor-based systems, set top boxes, programmable consumer electronics, network PCs, minicomputers, mainframe computers, distributed computing environments that include any of the above systems or devices, and the like. In a distributed computing environment, devices that perform the same or similar function may be viewed as being part of a "module" even if the devices are separate (whether local or remote) from each other.

The invention may be described in the general context of computer-executable instructions, such as program modules, being executed by a computer. Generally, program modules may include routines, programs, objects, components, data structures, etc., that perform particular tasks or store or process data structures, objects and other data types. The invention may also be practiced in distributed computing environments where tasks are performed by separate (local or remote) processing devices that are linked through a communications network. In a distributed computing environment, program modules may be located in both local and remote computer storage media including memory storage devices.

FIG. 3A shows illustrative wristband-sensor 300. A wristband worn comfortably on the arm may monitor dermatological characteristics, body temperature, blood pressure or any other suitable characteristic. Changes in body temperature or skin moistness may indicate emotional change.

FIG. 3B shows illustrative wristband 302. Illustrative wristband 302 may include one or more sensors 304. One or more of sensors 304 may sense temperature, audio pressure, or any other suitable physical signal. Wristband 302 may wirelessly transmits physiological data gathered to a remote or local processor device. Once physiological data has been captured, the comparison to known emotional indicators contained in the reference index may be performed in real time as the data stream is generated or physiological data may be stored and compared to the reference index at predetermined intervals.

FIG. 3C shows wristband 302 in place on a human wrist.

FIG. 4 shows an illustrative sensor that is embedded into a device that is regularly handled by the participant. Such devices may include, a mouse, touch screen, conventional writing instrument, stylus, telephone receiver or headset.

In FIG. 4, the device is illustrated as keyboard 400. The sensor is illustrated as temperature-sensitive film 402. Signal cable 404 is configured to transmit an electronic signal based on the temperature-response of temperature-sensitive film 402.

FIG. 5 shows an illustrative sensor in the form of a badge that may be worn by a participant. The badge may identify the wearer. The badge may measure physiological traits of an individual facing the wearer. The badge can concurrently measure physiological traits of the wearer as well. Data gathered by the badge may be transmitted to a remote or local computing device. In some embodiments, the badge itself may have sufficient computational power to perform all or some of the steps described in FIG. 1.

In FIG. 5, the badge is illustrated as badge 500. Badge 500 may include front surface 502, which may include text such as 504. Badge 500 may include back surface 508. Back surface 508 may support or be adjacent sensor 506. Sensor 506 may be an audio microphone. Sensor 506 may be in electronic communication with control module 510, which may include power, data storage, control, and any other suitable features.

Figure 6:
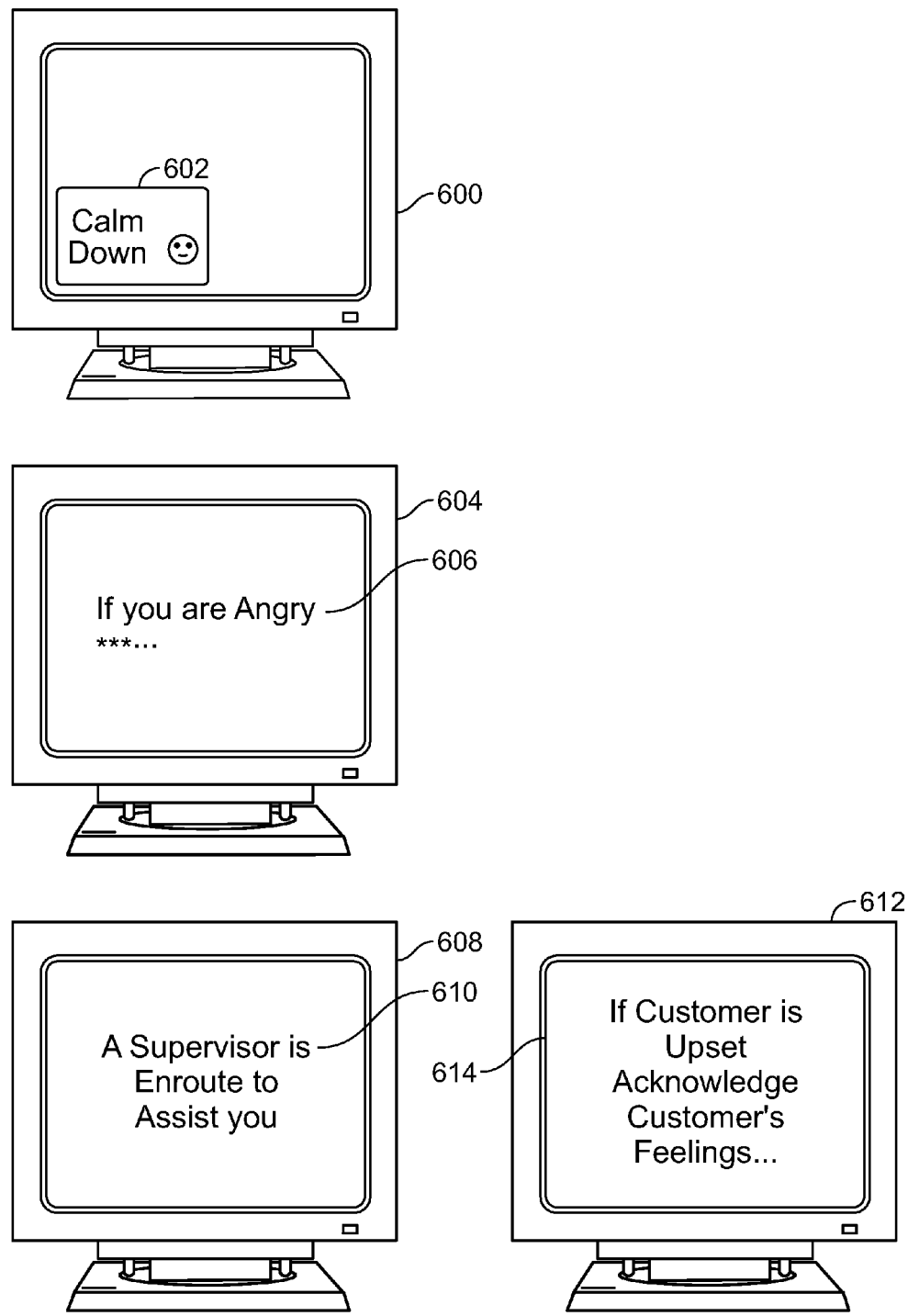
FIG. 6 shows yet further illustrative apparatus in accordance with the principles of the invention.

FIG. 6 shows illustrative screen shots depicting visual display of feedback information. The visual display may take the form of a pop up message or be part of an interactive chat dialogue.

In FIG. 6, the visual display is illustrated in connection with display 600, 604, 608 and 612, which show, respectively, text messages 602, 606, 610 and 614.

Thus, systems and methods for inducing a change in a performance characteristic have been provided. Persons skilled in the art will appreciate that the present invention can be practiced by other than the described embodiments, which are presented for purposes of illustration rather than of limitation. The present invention is limited only by the claims that follow.

What is claimed is:

1. A system for inducing a change in a performance characteristic comprising:
   a wearable badge having a sensor configured to sense the performance characteristic;
   a machine readable memory configured to store a performance characteristic reference index;

a processor device configured to provide a comparison of said sensed performance characteristic to said reference index; and a feedback channel configured to transmit feedback information based on said comparison to induce said change.

2. The system of claim 1 wherein said sensor includes a transmitter configured to transmit a wireless signal based on said performance characteristic.

3. The system of claim 1 wherein said sensor is configured to sense temperature.

4. The system of claim 3 wherein said performance characteristic reference index includes a logical link between a sensor output and an emotional state.

5. The system of claim 4 wherein said reference index includes a supplemental entry associated with said emotional state.

6. The system of claim 4 wherein said emotional state is associated with a change in a performance characteristic over time.

7. The system of claim 1 wherein said wearable badge includes an acoustic receiver.

8. A method for inducing a change in a performance characteristic of an individual, the method comprising:

using a receiver of a computer system, receiving from a wearable badge sensor an electronic signal corresponding to the performance characteristic; and using a processor of the computer system:
correlating the signal with a metric of the performance characteristic; and
linking the metric to an emotional state.

9. The method of claim 8 further comprising, using a transmitter of the computer system, providing to the individual feedback based on the emotional state.

10. The method of claim 8 wherein, when the individual is a first individual, the method further comprises, using the transmitter, providing to a second individual feedback based on the emotional state.

11. The method of claim 8 further comprising promoting a change in said performance characteristic.

12. The method of claim 11 wherein said promoting comprises applying biofeedback techniques.

13. The method of claim 11 wherein said promoting includes issuing to the individual an instruction to seek assistance.

14. The method of claim 11 wherein said promoting includes communicating via a real time textual chat dialogue.

15. One or more computer-readable media storing computer-executable instructions which, when executed by a processor on a computer system, perform a method for inducing a change in a performance characteristic of a first individual participating in a dialogue with a second individual, the method comprising:

receiving from a wearable badge sensor a signal corresponding to the performance characteristic;

correlating the signal with a metric of the performance characteristic;

linking the metric to an emotional state; and providing to the first individual feedback based on the emotional state, wherein the feedback comprises an instruction formulated to affect the first individual's participating in the dialogue.

16. The one or more media of claim 15 wherein, in the method, the linking comprises linking the metric to an emotion selected from the group consisting of happiness, sadness, fear, anger, disgust, contempt, and surprise.

17. The one or more media of claim 15 wherein the method further comprises transmitting said feedback to a third individual.

18. The one or more media of claim 15 wherein the feedback is formulated to induce a change in said performance characteristic.

19. The one or more media of claim 15 wherein the feedback is formulated using biofeedback techniques.

20. The one or more media of claim 15 wherein the providing comprises issuing to the first individual an instruction to seek assistance.

21. The one or more computer-readable media of claim 15 wherein, in the method, the providing comprises providing audible information.

* * * * *